United States Patent
Golebieski et al.

(10) Patent No.: US 10,064,649 B2
(45) Date of Patent: Sep. 4, 2018

(54) PLEATED SEAL FOR SURGICAL HAND OR INSTRUMENT ACCESS

(71) Applicant: Covidien LP, Mansfield, MA (US)

(72) Inventors: Kevin Golebieski, Prospect, CT (US); Greg Furnish, Louisville, KY (US); Benjamin Morris, Jeffersonville, IN (US); Wayne Johnson, Louisville, KY (US)

(73) Assignee: Covidien LP, Mansfield, MA (US)

( * ) Notice: Subject to any disclaimer, the term of this patent is extended or adjusted under 35 U.S.C. 154(b) by 41 days.

(21) Appl. No.: 14/740,353

(22) Filed: Jun. 16, 2015

(65) Prior Publication Data

US 2016/0000420 A1 Jan. 7, 2016

Related U.S. Application Data

(60) Provisional application No. 62/021,298, filed on Jul. 7, 2014.

(51) Int. Cl.
*A61B 1/32* (2006.01)
*A61B 17/34* (2006.01)
*A61B 17/02* (2006.01)

(52) U.S. Cl.
CPC ...... *A61B 17/3423* (2013.01); *A61B 17/0293* (2013.01); *A61B 17/3498* (2013.01); *A61B 2017/3435* (2013.01)

(58) Field of Classification Search
CPC ................... A61B 17/3423; A61B 2017/3425–2017/3429; A61B 2017/00265
See application file for complete search history.

(56) References Cited

U.S. PATENT DOCUMENTS

| | | |
|---|---|---|
| 2,468,985 A | 5/1949 | Krotz |
| 3,402,710 A | 9/1968 | Paleschuck |
| 3,495,586 A | 2/1970 | Regenbogen |
| 3,674,007 A | 7/1972 | Freis |
| 4,016,884 A | 4/1977 | Kwan-Gett |
| 4,112,932 A | 9/1978 | Chiulli |
| 4,183,357 A | 1/1980 | Bentley et al. |

(Continued)

FOREIGN PATENT DOCUMENTS

| | | |
|---|---|---|
| CA | 2702419 A1 | 11/2010 |
| EP | 0226026 A2 | 6/1987 |

(Continued)

*Primary Examiner* — Jacqueline Johanas

(57) ABSTRACT

A surgical access assembly for a surgical instrument and/or a surgeon's hand, the assembly including a housing, such as a wound retractor, and a seal body mounted to the housing. The seal body may have a pleated configuration when viewed in cross-section. The seal body may have a first surface and a second surface, the first surface having a plurality of radially-extending first channels and the second surface having a plurality of radially-extending second channels, the plurality of first channels being offset from the plurality of second channels. The seal body may define a substantially centrally disposed opening for reception of a hand/arm or instrument. In addition, the seal body may define one or more additional openings for simultaneous reception of an instrument and a hand.

19 Claims, 8 Drawing Sheets

(56) References Cited

U.S. PATENT DOCUMENTS

| | | |
|---|---|---|
| 4,356,826 A | 11/1982 | Kubota |
| 4,402,683 A | 9/1983 | Kopman |
| D276,937 S | 12/1984 | Griggs |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,197,955 A | 3/1993 | Stephens et al. |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,337,937 A | 8/1994 | Remiszewski et al. |
| 5,342,385 A * | 8/1994 | Norelli .............. A61B 17/02 604/104 |
| 5,345,927 A | 9/1994 | Bonutti |
| 5,350,364 A | 9/1994 | Stephens et al. |
| 5,360,417 A | 11/1994 | Gravener et al. |
| 5,366,478 A | 11/1994 | Brinkerhoff et al. |
| 5,375,588 A | 12/1994 | Yoon |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,443,452 A * | 8/1995 | Hart .............. A61B 17/3498 137/849 |
| 5,443,453 A | 8/1995 | Walker et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,556,387 A | 9/1996 | Mollenauer et al. |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,371,968 B1 | 4/2002 | Kogasaka et al. |
| 6,382,211 B1 | 5/2002 | Crook |

(56) References Cited

U.S. PATENT DOCUMENTS

| | | |
|---|---|---|
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,610,031 B1 * | 8/2003 | Chin ............... A61M 39/045 604/167.04 |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,706,050 B1 | 3/2004 | Giannadakis |
| 6,716,201 B2 | 4/2004 | Blanco |
| 6,718,628 B2 | 4/2004 | Munshi |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,981,966 B2 * | 1/2006 | Green ............... A61B 17/34 604/167.01 |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| D545,967 S | 7/2007 | Joyce et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,762,995 B2 | 7/2010 | Eversull et al. |
| 7,766,824 B2 | 8/2010 | Jensen et al. |
| 7,787,963 B2 | 8/2010 | Geistert et al. |
| 7,789,861 B2 * | 9/2010 | Franer ............... A61B 17/3462 604/167.01 |
| 7,798,898 B2 | 9/2010 | Luciano, Jr. et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 | 12/2010 | Piskun |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,951,076 B2 | 5/2011 | Hart et al. |
| 7,955,257 B2 | 6/2011 | Frasier et al. |
| 7,955,313 B2 | 6/2011 | Boismier |
| 7,988,671 B2 * | 8/2011 | Albrecht ............... A61B 17/3462 604/167.01 |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |

(56) References Cited

U.S. PATENT DOCUMENTS

| | | | |
|---|---|---|---|
| 8,092,430 B2 | 1/2012 | Richard et al. | |
| 8,105,234 B2 | 1/2012 | Ewers et al. | |
| 8,157,786 B2 | 4/2012 | Miller et al. | |
| 8,157,817 B2 | 4/2012 | Bonadio et al. | |
| 8,187,177 B2 | 5/2012 | Kahle et al. | |
| 8,187,178 B2 | 5/2012 | Bonadio et al. | |
| 8,226,553 B2 | 7/2012 | Shelton, IV et al. | |
| 8,251,900 B2 | 8/2012 | Ortiz et al. | |
| 8,257,252 B2 | 9/2012 | Kleyman | |
| 8,257,317 B2* | 9/2012 | Albrecht | A61B 17/3462 604/167.06 |
| 8,282,547 B2* | 10/2012 | Jensen | A61B 17/3423 600/208 |
| 8,308,639 B2* | 11/2012 | Albrecht | A61B 17/02 600/206 |
| 8,317,690 B2 | 11/2012 | Ransden et al. | |
| 8,323,184 B2 | 12/2012 | Spiegal et al. | |
| 8,328,761 B2 | 12/2012 | Widenhouse et al. | |
| 8,343,047 B2 | 1/2013 | Albrecht et al. | |
| 8,388,526 B2 | 3/2013 | Ewers et al. | |
| 8,394,018 B2 | 3/2013 | Piskun | |
| 8,414,485 B2 | 4/2013 | Richard et al. | |
| 8,465,494 B2 | 6/2013 | Butler et al. | |
| 8,480,683 B2 | 7/2013 | Fowler et al. | |
| 8,550,992 B2 | 10/2013 | Kleyman | |
| 8,574,153 B2 | 11/2013 | Richard | |
| 8,597,251 B2* | 12/2013 | Albrecht | A61B 17/3462 604/167.01 |
| 8,641,610 B2 | 2/2014 | Okoniewski et al. | |
| 8,668,641 B2 | 3/2014 | Smith | |
| 8,684,918 B2 | 4/2014 | Stopek | |
| 8,696,557 B2 | 4/2014 | Fischvogt | |
| 8,727,974 B2 | 5/2014 | Kasvikis | |
| 8,728,037 B2* | 5/2014 | Franer | A61B 17/3462 604/167.01 |
| 8,764,647 B2 | 7/2014 | Kleyman | |
| D712,033 S | 8/2014 | Richard et al. | |
| D712,034 S | 8/2014 | Richard et al. | |
| 8,795,164 B2 | 8/2014 | Stopek | |
| 9,017,254 B2* | 4/2015 | Brustad | A61B 17/02 600/206 |
| D736,921 S | 8/2015 | Richard et al. | |
| 9,149,294 B2* | 10/2015 | Webb | A61M 39/0247 |
| 9,314,269 B2* | 4/2016 | Webb | A61B 17/3462 |
| 9,398,924 B2* | 7/2016 | Webb | A61B 17/3421 |
| 2001/0037053 A1 | 11/2001 | Bonadio et al. | |
| 2002/0055714 A1 | 5/2002 | Rothschild | |
| 2003/0014076 A1 | 1/2003 | Mollenauer et al. | |
| 2003/0093104 A1 | 5/2003 | Bonner et al. | |
| 2003/0212383 A1 | 11/2003 | Cote et al. | |
| 2004/0059297 A1 | 3/2004 | Racenet et al. | |
| 2004/0092795 A1 | 5/2004 | Bonadio et al. | |
| 2004/0102804 A1 | 5/2004 | Chin | |
| 2004/0111061 A1 | 6/2004 | Curran | |
| 2004/0127772 A1* | 7/2004 | Ewers | A61B 1/06 600/212 |
| 2004/0138529 A1 | 7/2004 | Wiltshire et al. | |
| 2004/0204734 A1 | 10/2004 | Wagner et al. | |
| 2004/0267096 A1 | 12/2004 | Caldwell et al. | |
| 2005/0020884 A1 | 1/2005 | Hart et al. | |
| 2005/0070935 A1 | 3/2005 | Ortiz | |
| 2005/0096695 A1 | 5/2005 | Olich | |
| 2005/0119525 A1 | 6/2005 | Takemoto | |
| 2005/0137459 A1 | 6/2005 | Chin et al. | |
| 2005/0148823 A1 | 7/2005 | Vaugh et al. | |
| 2005/0192483 A1 | 9/2005 | Bonadio et al. | |
| 2005/0203346 A1 | 9/2005 | Bonadio et al. | |
| 2005/0203467 A1* | 9/2005 | O'Heeron | A61B 17/3498 604/249 |
| 2005/0209608 A1 | 9/2005 | O'Heeron | |
| 2005/0245876 A1 | 11/2005 | Khosravi et al. | |
| 2005/0251092 A1 | 11/2005 | Howell et al. | |
| 2005/0277946 A1 | 12/2005 | Greenhalgh | |
| 2005/0288634 A1* | 12/2005 | O'Heeron | A61B 17/3462 604/167.06 |
| 2006/0071432 A1 | 4/2006 | Staudner | |
| 2006/0129165 A1 | 6/2006 | Edoga et al. | |
| 2006/0149137 A1 | 7/2006 | Pingleton et al. | |
| 2006/0149306 A1 | 7/2006 | Hart et al. | |
| 2006/0161049 A1 | 7/2006 | Beane et al. | |
| 2006/0161050 A1 | 7/2006 | Butler et al. | |
| 2006/0212063 A1 | 9/2006 | Wilk | |
| 2006/0220325 A1* | 10/2006 | McFarlane | A61B 17/3462 277/607 |
| 2006/0224161 A1 | 10/2006 | Bhattacharyya | |
| 2006/0241651 A1 | 10/2006 | Wilk | |
| 2006/0247500 A1 | 11/2006 | Voegele et al. | |
| 2006/0247516 A1 | 11/2006 | Hess et al. | |
| 2006/0247586 A1 | 11/2006 | Voegele et al. | |
| 2006/0247673 A1 | 11/2006 | Voegele et al. | |
| 2006/0247678 A1 | 11/2006 | Weisenburgh et al. | |
| 2006/0270911 A1 | 11/2006 | Voegele et al. | |
| 2007/0118175 A1 | 5/2007 | Butler et al. | |
| 2007/0203398 A1 | 8/2007 | Bonadio et al. | |
| 2007/0208312 A1 | 9/2007 | Norton et al. | |
| 2007/0255218 A1* | 11/2007 | Franer | A61B 17/3462 604/167.02 |
| 2007/0270654 A1 | 11/2007 | Pignato et al. | |
| 2007/0270882 A1 | 11/2007 | Hjelle et al. | |
| 2008/0027476 A1 | 1/2008 | Piskun | |
| 2008/0048011 A1 | 2/2008 | Weller | |
| 2008/0097162 A1 | 4/2008 | Bonadio et al. | |
| 2008/0097332 A1 | 4/2008 | Greenhalgh et al. | |
| 2008/0146883 A1* | 6/2008 | Kistler | A61B 17/3423 600/207 |
| 2008/0161826 A1 | 7/2008 | Guiraudon | |
| 2008/0194973 A1 | 8/2008 | Imam | |
| 2008/0255519 A1 | 10/2008 | Piskun et al. | |
| 2008/0319261 A1 | 12/2008 | Lucini et al. | |
| 2009/0012477 A1 | 1/2009 | Norton et al. | |
| 2009/0036738 A1 | 2/2009 | Cuschieri et al. | |
| 2009/0093752 A1 | 4/2009 | Richard et al. | |
| 2009/0093850 A1 | 4/2009 | Richard | |
| 2009/0105635 A1 | 4/2009 | Bettuchi et al. | |
| 2009/0131751 A1 | 5/2009 | Spivey et al. | |
| 2009/0182279 A1 | 7/2009 | Wenchell et al. | |
| 2009/0182288 A1 | 7/2009 | Spenciner | |
| 2009/0204067 A1 | 8/2009 | Abu-Halawa | |
| 2009/0227843 A1 | 9/2009 | Smith et al. | |
| 2009/0299292 A1 | 12/2009 | Renaux | |
| 2009/0326330 A1 | 12/2009 | Bonadio et al. | |
| 2009/0326332 A1 | 12/2009 | Carter | |
| 2010/0063452 A1 | 3/2010 | Edelman et al. | |
| 2010/0100043 A1 | 4/2010 | Racenet | |
| 2010/0113886 A1 | 5/2010 | Piskun et al. | |
| 2010/0228094 A1 | 9/2010 | Ortiz et al. | |
| 2010/0240960 A1 | 9/2010 | Richard | |
| 2010/0249516 A1 | 9/2010 | Shelton, IV et al. | |
| 2010/0261975 A1 | 10/2010 | Huey et al. | |
| 2010/0280326 A1 | 11/2010 | Hess et al. | |
| 2010/0286484 A1 | 11/2010 | Stellon et al. | |
| 2010/0286506 A1 | 11/2010 | Ransden et al. | |
| 2010/0298646 A1 | 11/2010 | Stellon et al. | |
| 2011/0009704 A1 | 1/2011 | Marczyk et al. | |
| 2011/0021877 A1 | 1/2011 | Fortier et al. | |
| 2011/0028891 A1 | 2/2011 | Okoniewski | |
| 2011/0054257 A1 | 3/2011 | Stopek | |
| 2011/0054258 A1 | 3/2011 | O'Keefe et al. | |
| 2011/0054260 A1 | 3/2011 | Albrecht et al. | |
| 2011/0082341 A1 | 4/2011 | Kleyman et al. | |
| 2011/0082343 A1 | 4/2011 | Okoniewski | |
| 2011/0082346 A1 | 4/2011 | Stopek | |
| 2011/0118553 A1 | 5/2011 | Stopek | |
| 2011/0124968 A1 | 5/2011 | Kleyman | |
| 2011/0124969 A1 | 5/2011 | Stopek | |
| 2011/0124970 A1 | 5/2011 | Kleyman | |
| 2011/0125186 A1 | 5/2011 | Fowler et al. | |
| 2011/0166423 A1 | 7/2011 | Farascioni et al. | |
| 2011/0251463 A1 | 10/2011 | Kleyman | |
| 2011/0251464 A1 | 10/2011 | Kleyman | |
| 2011/0251465 A1 | 10/2011 | Kleyman | |
| 2011/0251466 A1 | 10/2011 | Kleyman et al. | |

(56) References Cited

U.S. PATENT DOCUMENTS

| | | | |
|---|---|---|---|
| 2011/0251560 A1* | 10/2011 | Albrecht | A61B 17/3462 604/167.01 |
| 2011/0313250 A1 | 12/2011 | Kleyman | |
| 2012/0004613 A1* | 1/2012 | Franer | A61B 17/3462 604/167.03 |
| 2012/0059640 A1 | 3/2012 | Roy et al. | |
| 2012/0130177 A1 | 5/2012 | Davis | |
| 2012/0130179 A1 | 5/2012 | Rockrohr | |
| 2012/0130181 A1 | 5/2012 | Davis | |
| 2012/0130182 A1 | 5/2012 | Rodrigues, Jr. et al. | |
| 2012/0130183 A1 | 5/2012 | Barnes | |
| 2012/0130184 A1 | 5/2012 | Richard | |
| 2012/0130185 A1 | 5/2012 | Pribanic | |
| 2012/0130186 A1 | 5/2012 | Stopek et al. | |
| 2012/0130187 A1 | 5/2012 | Okoniewski | |
| 2012/0130188 A1 | 5/2012 | Okoniewski | |
| 2012/0130190 A1 | 5/2012 | Kasvikis | |
| 2012/0130191 A1 | 5/2012 | Pribanic | |
| 2012/0149987 A1 | 6/2012 | Richard et al. | |
| 2012/0157777 A1 | 6/2012 | Okoniewski | |
| 2012/0157779 A1 | 6/2012 | Fischvogt | |
| 2012/0157780 A1 | 6/2012 | Okoniewski et al. | |
| 2012/0157781 A1 | 6/2012 | Kleyman | |
| 2012/0157782 A1 | 6/2012 | Alfieri | |
| 2012/0157783 A1 | 6/2012 | Okoniewski et al. | |
| 2012/0157784 A1 | 6/2012 | Kleyman et al. | |
| 2012/0157785 A1 | 6/2012 | Kleyman | |
| 2012/0157786 A1 | 6/2012 | Pribanic | |
| 2012/0190931 A1 | 7/2012 | Stopek | |
| 2012/0190932 A1 | 7/2012 | Okoniewski | |
| 2012/0190933 A1 | 7/2012 | Kleyman | |
| 2012/0209077 A1 | 8/2012 | Racenet | |
| 2012/0245425 A1 | 9/2012 | Okoniewski | |
| 2012/0253134 A1 | 10/2012 | Smith | |
| 2012/0316501 A1* | 12/2012 | Albrecht | A61B 17/3462 604/167.03 |
| 2013/0178708 A1 | 7/2013 | Malkowski et al. | |
| 2013/0184646 A1 | 7/2013 | Richard et al. | |
| 2013/0225931 A1 | 8/2013 | Cruz et al. | |
| 2013/0245373 A1 | 9/2013 | Okoniewski | |
| 2013/0253277 A1 | 9/2013 | Smith | |
| 2013/0253278 A1 | 9/2013 | Smith | |
| 2013/0274559 A1 | 10/2013 | Fowler et al. | |
| 2013/0310651 A1 | 11/2013 | Alfieri | |
| 2014/0039268 A1 | 2/2014 | Richard | |
| 2014/0051933 A1 | 2/2014 | Okoniewski | |
| 2014/0121466 A1 | 5/2014 | Okoniewski et al. | |
| 2014/0142392 A1 | 5/2014 | Smith | |
| 2014/0171745 A1 | 6/2014 | Stopek | |
| 2014/0316338 A1* | 10/2014 | Franer | A61B 17/3462 604/167.03 |
| 2015/0038796 A1 | 2/2015 | Okoniewski | |

FOREIGN PATENT DOCUMENTS

| | | |
|---|---|---|
| EP | 0538060 A1 | 4/1993 |
| EP | 630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2095781 A2 | 9/2009 |
| EP | 2098182 A2 | 9/2009 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2292165 | 3/2011 |
| EP | 2343019 | 7/2011 |
| GB | 2469083 | 4/2009 |
| WO | 84/01512 | 4/1984 |
| WO | 93/14801 | 8/1993 |
| WO | 94/04067 | 3/1994 |
| WO | 96/10963 | 4/1996 |
| WO | 96/36283 | 11/1996 |
| WO | 97/33520 | 9/1997 |
| WO | 97/42889 A1 | 11/1997 |
| WO | 99/16368 | 4/1999 |
| WO | 99/22804 | 5/1999 |
| WO | 00/32116 | 6/2000 |
| WO | 00/32120 | 6/2000 |
| WO | 01/08581 | 2/2001 |
| WO | 01/49363 | 7/2001 |
| WO | 02/07611 | 1/2002 |
| WO | 03/034908 A2 | 5/2003 |
| WO | 03/071926 | 9/2003 |
| WO | 2004/043275 | 5/2004 |
| WO | 2004/054456 | 7/2004 |
| WO | 2004/075741 A2 | 9/2004 |
| WO | 2004/075930 | 9/2004 |
| WO | 2005/058409 | 6/2005 |
| WO | 2006/019723 | 2/2006 |
| WO | 2006/100658 A2 | 9/2006 |
| WO | 2006/110733 | 10/2006 |
| WO | 2007/018458 | 2/2007 |
| WO | 2007/095703 | 8/2007 |
| WO | 2007/143200 | 12/2007 |
| WO | 2008/015566 A2 | 2/2008 |
| WO | 2008/042005 | 4/2008 |
| WO | 2008/077080 | 6/2008 |
| WO | 2008/093313 | 8/2008 |
| WO | 2008/103151 | 8/2008 |
| WO | 2008/121294 A1 | 10/2008 |
| WO | 2009/036343 | 3/2009 |
| WO | 2010/141409 | 12/2010 |

\* cited by examiner

PLEATED SEAL FOR SURGICAL HAND OR INSTRUMENT ACCESS

CROSS-REFERENCE TO RELATED APPLICATIONS

This application claims the benefit of and priority to U.S. Provisional Patent Application No. 62/021,298, filed Jul. 7, 2014, the entire disclosure of which is incorporated by reference herein.

TECHNICAL FIELD

The present application is directed to devices for providing sealed access of a hand or instrument plugs for use in surgical procedures and, more particularly, to access surgical site seal covers or plugs that improve a surgical seal while providing greater flexibility.

SUMMARY

The present disclosure, according to various embodiments thereof, relates to a hand or instrument access assembly comprising a housing and a seal body mounted to the housing, the seal body having a first surface and a second surface, the seal body defining a substantially centrally disposed opening therethrough, wherein the first surface has a plurality of radially-extending first channels and the second surface has a plurality of radially-extending second channels, the plurality of first channels being offset from the plurality of second channels.

The plurality of first channels may have a first width and the plurality of second channels may have a second width, the first width being equal to the second width or the first width being different than the second width. The plurality of first channels and the plurality of second channels may each form a star-shaped configuration. The plurality of first channels and the plurality of second channels may extend partially along the radius of the seal. One end of each of the plurality of first channels and one end of each of the plurality of second channels may converge at the opening.

In various embodiments, when a hand or an instrument is inserted through the opening, the plurality of first channels and the plurality of second channels deform in an accordion-like manner to accommodate the hand or the instrument. The seal may be formed of foam, e.g., a monolithic piece of foam.

The housing may be a wound retractor. The wound retractor may include a distal ring for positioning through an incision for placement inside a body wall and against an interior surface of a body wall, a proximal ring for positioning outside of the body wall and a flexible sleeve connecting the distal and proximal rings, the sleeve configured to be rolled around the proximal ring so as to shorten the length of the sleeve and thereby generate a retraction force to retract the incision. In addition, the housing may also include a stiffening ring that assists with maintaining the proximal ring in a circular shape, the seal mounting directly to the stiffening ring.

The opening may be closed in a rest position so as to prevent the escape of insufflation gas therethrough when no hand or instrument is inserted. The seal body may also have one or more additional openings for sealed reception of an instrument therethrough. At least a portion of the one or more additional openings may be molded so as to be closed until reception of an instrument therethrough tears the material to fully form the opening. At least a portion of the one or more additional openings may include a pre-formed slit that, in a rest position, is closed.

The present disclosure, according to various embodiments thereof, may also relate to a hand access assembly for performing a laparoscopic surgical procedure, the assembly comprising a housing, and a seal body mounted to the housing and defining an opening therethrough for reception of a hand, the seal body having a pleated configuration. The pleated configuration may include a plurality of first and second channels positioned on opposite sides of the seal body, and may be offset relative to each other. The plurality of first channels may have a first width and the plurality of second channels have a second width, the first width being equal to the second width or the first width being different than the second width. The plurality of first channels and the plurality of second channels may each form a star-shaped configuration. The plurality of first channels and the plurality of second channels may extend partially along the radius of the seal. One end of each of the plurality of first channels and one end of each of the plurality of second channels may converge at the opening.

In various embodiments, when a hand or an instrument is inserted through the opening, the plurality of first channels and the plurality of second channels deform in an accordion-like manner to accommodate the hand or the instrument. The seal may be formed of foam, e.g., a monolithic piece of foam.

The housing may be a wound retractor. The wound retractor may include a distal ring for positioning through an incision for placement inside a body wall and against an interior surface of a body wall, a proximal ring for positioning outside of the body wall and a flexible sleeve connecting the distal and proximal rings, the sleeve configured to be rolled around the proximal ring so as to shorten the length of the sleeve and thereby generate a retraction force to retract the incision. In addition, the housing may also include a stiffening ring that assists with maintaining the proximal ring in a circular shape, the seal mounting directly to the stiffening ring.

The opening may be closed in a rest position so as to prevent the escape of insufflation gas therethrough when no hand or instrument is inserted. The seal body may also have one or more additional openings for sealed reception of an instrument therethrough. At least a portion of the one or more additional openings may be molded so as to be closed until reception of an instrument therethrough tears the material to fully form the opening. At least a portion of the one or more additional openings may include a pre-formed slit that, in a rest position, is closed.

The present disclosure, according to various embodiments thereof, may also relate to a hand or surgical instrument access assembly comprising a wound retractor, wherein the wound retractor includes a distal ring for positioning through an incision for placement inside a body wall and against an interior surface of a body wall, a proximal ring for positioning outside of the body wall and a flexible sleeve connecting the distal and proximal rings, the sleeve configured to be rolled around the proximal ring so as to shorten the length of the sleeve and thereby generate a retraction force to retract the incision; a stiffening ring for maintaining the proximal ring in a circular shape; and a seal body mounted to the stiffening ring, the seal body defining an opening therethrough for reception of a surgical instrument or hand, wherein the seal body has a pleated configuration.

The pleated configuration may include a plurality of first and second channels positioned on opposite sides of the seal body, and may be offset relative to each other. The plurality of first channels may have a first width and the plurality of second channels have a second width, the first width being equal to the second width or the first width being different than the second width. The plurality of first channels and the plurality of second channels may each form a star-shaped configuration. The plurality of first channels and the plurality of second channels may extend partially along the radius of the seal. One end of each of the plurality of first channels and one end of each of the plurality of second channels may converge at the opening.

In various embodiments, when a hand or an instrument is inserted through the opening, the plurality of first channels and the plurality of second channels deform in an accordion-like manner to accommodate the hand or the instrument. The seal may be formed of foam, e.g., a monolithic piece of foam.

The housing may be a wound retractor. The wound retractor may include a distal ring for positioning through an incision for placement inside a body wall and against an interior surface of a body wall, a proximal ring for positioning outside of the body wall and a flexible sleeve connecting the distal and proximal rings, the sleeve configured to be rolled around the proximal ring so as to shorten the length of the sleeve and thereby generate a retraction force to retract the incision. In addition, the housing may also include a stiffening ring that assists with maintaining the proximal ring in a circular shape, the seal mounting directly to the stiffening ring.

The opening may be closed in a rest position so as to prevent the escape of insufflation gas therethrough when no hand or instrument is inserted. The seal body may also have one or more additional openings for sealed reception of an instrument therethrough. At least a portion of the one or more additional openings may be molded so as to be closed until reception of an instrument therethrough tears the material to fully form the opening. At least a portion of the one or more additional openings may include a pre-formed slit that, in a rest position, is closed.

Further scope of applicability of the present disclosure will become apparent from the detailed description given hereinafter. However, it should be understood that the detailed description and specific examples, while indicating illustrative embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1:
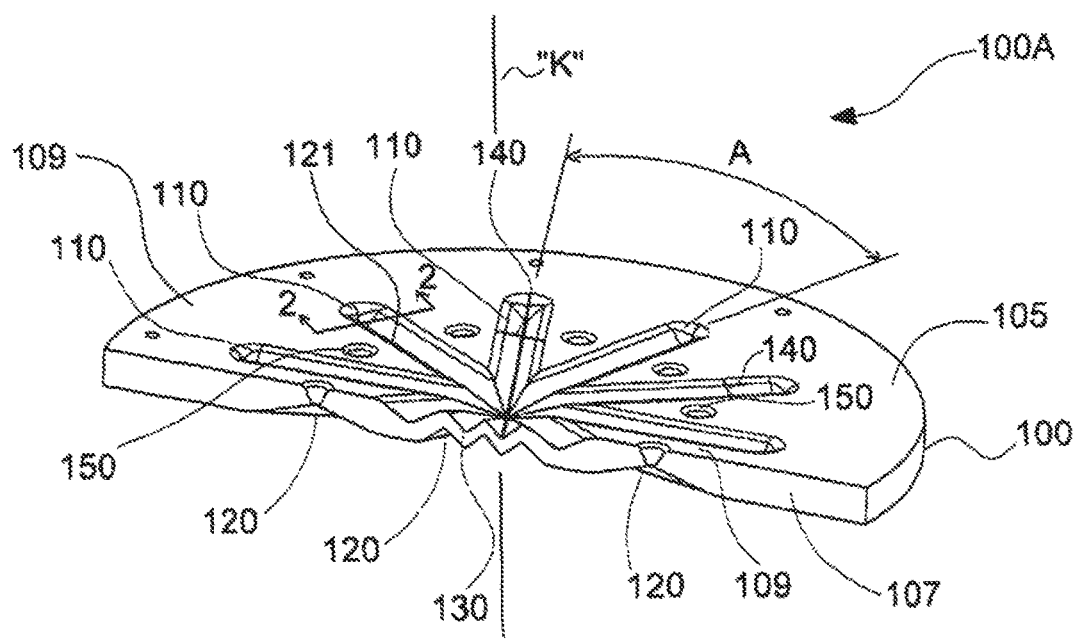
FIG. 1 is a perspective view in partial cross-section of a hand or instrument access surgical site seal cover or plug according to one exemplary embodiment of the present disclosure, including a pleated seal having a plurality of first and second channels on respective first top and second bottom sides of the pleated seal.

Particular embodiments of the present disclosure will be described herein with reference to the accompanying drawings. As shown in the drawings and as described throughout the following description, and as is traditional when referring to relative positioning on an object, the term "proximal" refers to the end of the laparoscopic sealing cover or plug that is closer to the user and the term "distal" refers to the end of the laparoscopic sealing cover or plug that is further from the user.

The laparoscopic sealing covers or plugs of the present disclosure, according to various embodiments thereof, include sealable openings that receive various types of instrumentation or objects (e.g., a hand of a user) while maintaining a fluid tight seal about the instrumentation or hand to prevent the loss of insufflation pressure within a laparoscopic surgical site. In addition, the laparoscopic sealing covers or plugs of the present disclosure, according to various embodiments thereof, maintain insufflation pressure within a laparoscopic surgical site when no instrumentation or objects are introduced, the sealable openings thereby providing a zero seal. The laparoscopic sealing covers or plugs accommodate angular manipulation of the hand, arm or a surgical instrument. The sealable openings may prevent the escape of insufflation gas from the body cavity, as well as prevent the entry of undesirable foreign matter into the body cavity. Examples of instrumentation include trocars, clip appliers, graspers, dissectors, retractors, staplers, laser probes, photographic devices, endoscopes and laparoscopes, tubes, and the like.

The present disclosure relates to various embodiments of hand/or instrument access surgical site seal covers or plugs that enable sealed access to a surgical site with either a surgeon's hand and/or one or more instruments.

A surgical site may include an opening or incision in a patient or a natural orifice through which a surgical procedure may be performed.

FIGS. 1-4 illustrate an exemplary embodiment of the present invention. The laparoscopic sealing cover or plug may be mounted to a housing, such as a wound retractor or a separate stiffening ring used in combination with a wound refractor. The laparoscopic sealing cover or plug 100A includes a seal body 100 defining a central longitudinal axis "k" and a central seal passage or opening 130 in general longitudinal alignment with the central longitudinal axis "k". The seal body 100 has a first top (e.g., proximal) side or surface 105 and an opposed second bottom (e.g., distal) side or surface 107. The laparoscopic sealing cover or plug 100 has a plurality of first grooves or channels 110 disposed on the top surface 105 and a plurality of second grooves or channels 120 disposed on the bottom surface 107. The first and second channels 110, 120 do not extend fully through the seal body 100 but rather extend partially from therethrough. The plurality of second channels 120 are more clearly depicted in FIG. 3, which is a bottom view of the laparoscopic sealing cover or plug 100A. The laparoscopic sealing cover or plug 100A is illustrated as being flat, although it may have a domed or other suitable shape. A plurality of different materials may be used to form or construct the laparoscopic sealing cover or plug 100A, as discussed below in further detail.

Figure 2:
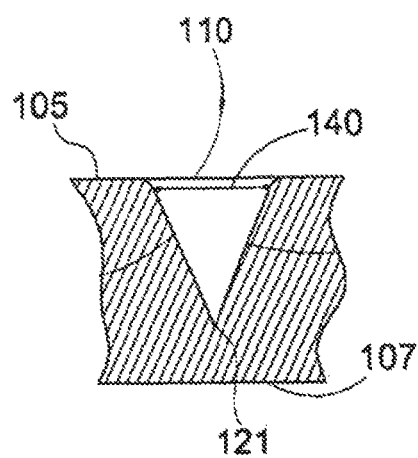
FIG. 2 is an enlarged cross-sectional view taken along the lines 2-2 of FIG. 1 illustrating the configuration of the first and second channels.

Each of the first and second channels 110, 120 may be generally V-shaped, as best depicted in FIG. 2, or U-shaped, having a first width or dimension 140 at or near the exterior surface of the laparoscopic sealing cover or plug, the first width or dimension 140 gradually decreasing toward the interior of the seal body 100 and terminating at a bottom surface 121. The first and second channels 110, 120 may be substantially identical in their respective cross-sectional shapes or dimensions, or, in the alternative, may have different cross-sectional shapes or dimensions. Referring to the embodiment shown herein, the V-shape of the second channels 120 is inverted relative to the V-shape of the first channel 110 due to their arrangement on the opposite side of surface of the laparoscopic sealing cover or plug 100A. In an embodiment, the top surface 105 has ten channels (see FIG. 1) and the bottom surface 107 also has 10 channels (see FIG. 3). However, any number of channels may be located on either the top or bottom surfaces 105, 107, such as, for example, 5 through 20 channels per side. In the embodiment shown, the first and second channels 110, 120 do not extend fully to the outer perimeter of the laparoscopic sealing cover or plug 100A (or along the entire radius of the laparoscopic sealing cover or plug 100A). Instead, the first and second channels 110, 120 extend about ¾ of the radius of the laparoscopic sealing cover or plug 100A. The first and second channels 110, 120 each extend radially outwardly relative to the longitudinal axis "k", and may or may not be coterminous with the central seal passage 130. The first and second channels 110, 120 form star-shaped configurations on the top surface 105 and the bottom surface 107, respectively. As illustrated, the plurality of first channels 110 are arranged in a circumferential manner and the plurality of second channels 120 are also arranged in a circumferential manner. The plurality of first channels 110 may form a first pattern on the top surface 105 and the plurality of second channels 120 may form a second pattern on the bottom surface 107. In the exemplary embodiments described herein, the first and second patterns are similar.

Figure 3:
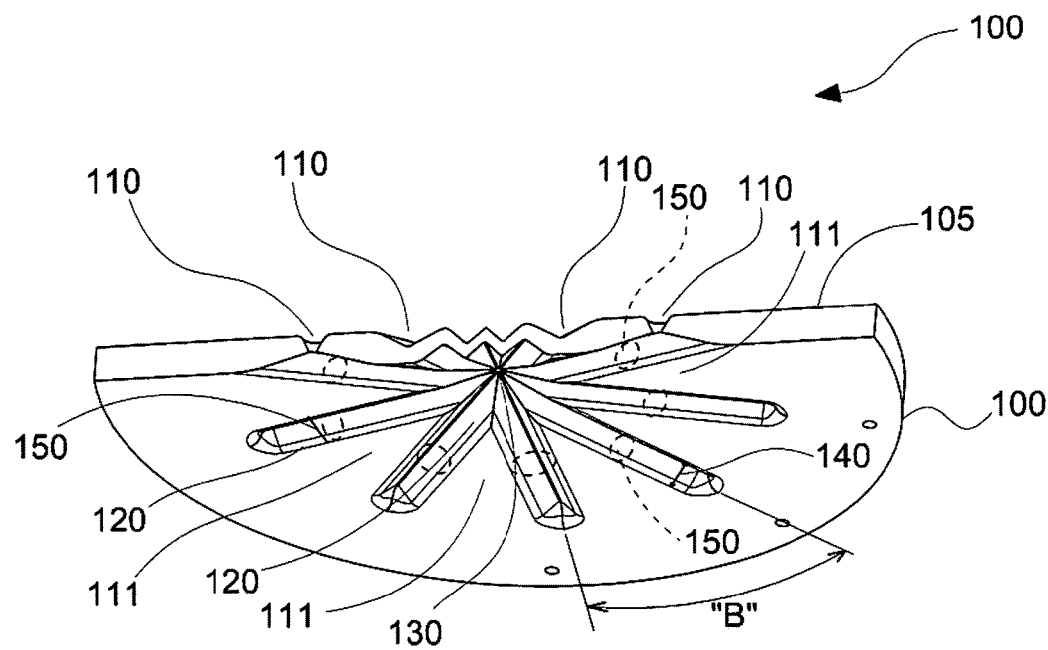
FIG. 3 is a perspective view in partial cross-section illustrating the second side of the pleated seal and the second channels.

Adjacent first channels 110 are separated by wedge segments 109 of the seal body 100 (FIG. 1) and adjacent second channels 120 are separated by wedge segments 111 of the seal body 100 (FIG. 3). This arrangement of alternating channels and wedge segments, offset on opposite sides of the laparoscopic sealing cover or plug 100A, provides an undulating or corrugated structure in cross-section so as to form pleats, such structure increasing the structural integrity of the laparoscopic sealing cover or plug 100A while enabling the laparoscopic sealing cover or plug 100A to accommodate stretching and deformation during passage of an instrument or a clinician's hand and arm.

In an embodiment, the first channels 110 are equidistantly spaced relative to each other at a first predefined angular displacement "A" and the second channels 120 are equidistantly spaced relative to each other at a second predefined angular displacement "B." In an embodiment having the same number of first and second channels 110, 120, the first and second predefined angular displacements "A", "B" may be substantially equal. For example, in an embodiment having ten first and second channels 110, 120 on the top and bottom surfaces 105, 107, the angular displacement "A", "B" is about 36 degrees. In other embodiments, the first and second channels 110, 120 may have varying angular displacements. Furthermore, while the first and second channels 110, 120 are each straight in the embodiments shown and described herein, in still other embodiments, the first and second channels 110, 120 may define a shape other than straight, e.g., curved, angled, etc.

Figure 4:
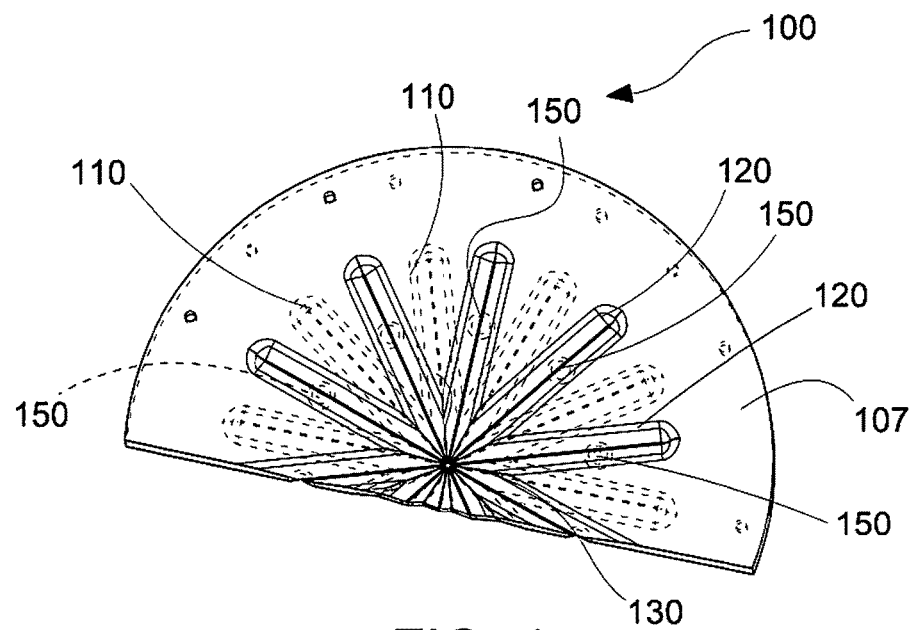
FIG. 4 is a top plan view of the pleated seal illustrating the radial displacement of the first and second channels with the second channels being shown in phantom.

With reference to FIG. 4, the first and second channels 110, 120 may be angularly offset or displaced with respect to each other. In FIG. 4, the second channels 120 are depicted in phantom. In an embodiment, the second channels 120 are angularly offset to bisect adjacent first channels 110, e.g., the second channels 120 are arranged along the midline separating adjacent first channels 110, e.g., along the midline of the wedge segment 109. The first channels 110 are angularly offset to bisect adjacent second channels 120, e.g., the first channels 110 are arranged along the midline separating adjacent second channels 120, e.g., along the midline of the wedge segment 111. This arrangement adds to the structural integrity of the seal body 100 by ensuring that the thickness beneath each of the first channels 110 and above each of the second channels 120 is sufficient to withstand stretching of the seal body during passage of the arm or hand of the clinician without the laparoscopic sealing cover or plug 100A inadvertently tearing.

Referring to FIG. 1, opening 130 is shown adjacent the center of top surface 105. In the embodiment shown, the opening 130 is configured to receive a hand and/or arm of a user (e.g., a surgeon). In addition, FIG. 1 illustrates a plurality of additional openings 150 (although any number of such openings, e.g., one or more, may be employed). Openings 150 are located on the top surface of the laparoscopic sealing cover or plug 100A and advantageously are positioned such that their uppermost portion (the portion that is co-planar with the top surface of the laparoscopic sealing cover or plug 100A) is located in a respective wedge section of the top surface, and such that their lowermost portion (the portion that is co-planar with the bottom surface of the laparoscopic sealing cover or plug 100A) is located in a respective channel 120 of the bottom surface. In an embodiment, the openings 150 taper from the top surface of the laparoscopic sealing cover or plug 100A to the bottom surface of the laparoscopic sealing cover or plug 100A. In this manner, the openings 150 have a relatively large diameter at the top surface, allowing a surgeon to easily locate and place an instrument therethrough, and a relatively small diameter at the bottom surface, providing for an improved seal. In an embodiment, the openings 150 may, in a rest position of the laparoscopic sealing cover or plug 100A, be open. Alternatively, in other embodiments, the openings 150 may, in a rest position of the laparoscopic sealing cover or plug 100A, be closed so as to provide a zero seal when an instrument is not present therethrough. In such an embodiment, the laparoscopic sealing cover or plug 100A may be molded such that the material that forms the lowermost portion of the openings 150 forms a thin barrier that prevents passage of insufflation gases, the thin barrier being puncturable by an instrument inserted therethrough. Alternatively, the laparoscopic sealing cover or plug 100A may be molded such that the material that forms the lowermost portion of the openings 150 has a pre-formed hole or slit therethrough, the hole or slit being pressed closed during use so as to prevent passage of insufflation gases. Any number of openings 150 may be employed, so as to enable simultaneous sealed access of both a hand/arm (through the opening 130) and an instrument (through the openings 150).

The laparoscopic sealing cover or plug 100A may be constructed of rigid materials or alternatively made from a disposable, pliable, compressible, and/or flexible type material, for example, but not limited to, a suitable foam material having sufficient compliance to form a seal about one or more surgical objects. In one embodiment, the foam may be at least partially constituted of polyisoprene, urethane, or silicone, or the like. Moreover, the laparoscopic sealing cover or plug 100A may be formed of a medical grade plastic or medical grade foam or, e.g., latex, silicone rubber, Mylar®, polyethylene, polyurethane, a flexible polymeric material, or a composite material, such as a polyethylene and nylon composite, or any other resilient material suitable for the intended purpose of permitting insertion and manipulation, e.g., off-axis manipulation, of a surgical instrument or clinician's hand.

Figure 5:
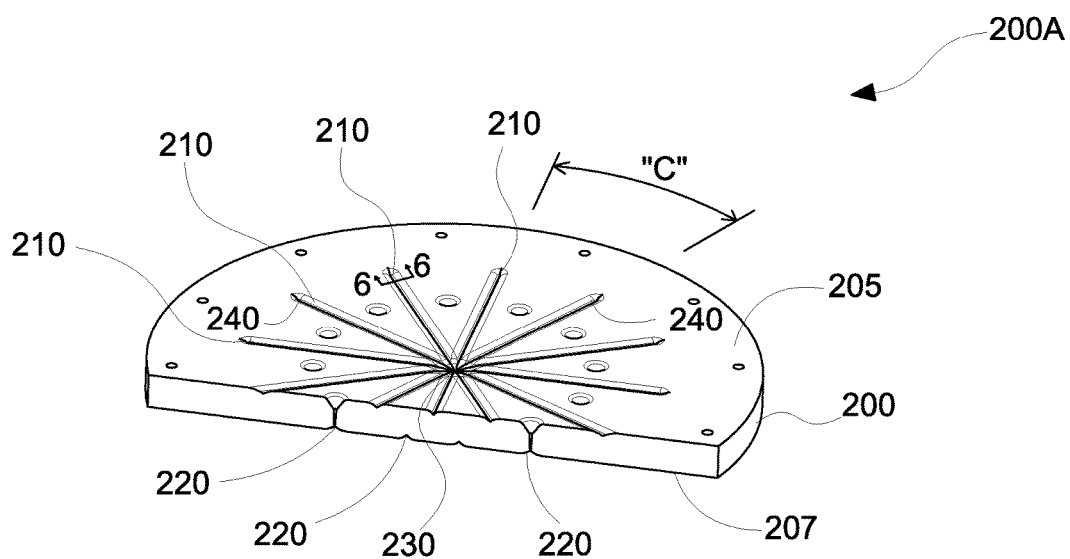
FIG. 5 is a perspective view in partial cross-section of a hand or instrument access surgical site seal cover or plug according to another exemplary embodiment of the present disclosure.

FIG. 5 illustrates a top view of a laparoscopic sealing cover or plug 200, according to another exemplary embodiment of the present disclosure. The laparoscopic sealing cover or plug 200 is generally similar to the seal 100 described with reference to FIGS. 1-4, except that the plurality of first channels 210 and the plurality of second channels 220 are twelve in number. Thus, the first channels 210 may be angularly displaced at an angle "C" of about 30 degrees. Similarly, the second channels 120 may be angularly displaced at an angle "D" of about 30 degrees. Other symmetrical and non-symmetrical arrangements are envisioned as well. In addition, similar to the embodiment of FIGS. 1-4, the first and second channels 210, 220 are radially offset with respect to each other, e.g., when viewing the laparoscopic sealing cover or plug 200 in plan view, to bisect adjacent first and second channels 210, 220 as discussed hereinabove.

Figure 6:
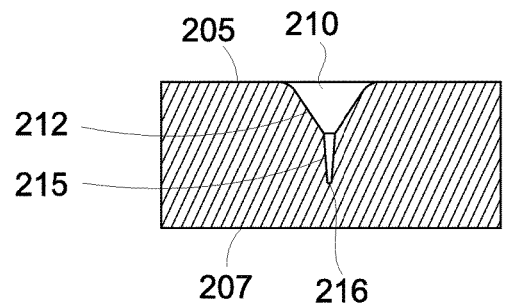
FIG. 6 is an enlarged cross-sectional view taken along the lines 6-6 of FIG. 5 illustrating the configuration of the first and second channels of FIG. 5.

As best depicted in FIG. 6, the first and second channels 210, 220 may each define cross-sectional dimensions that differ at varying depths thereof. For example, the first and second channels 210, 220 each define a first, relatively wider V-shaped segment 212 adjacent the respective top and bottom surfaces of the seal 200 and a second, relatively narrower segment 215 extending therefrom farther into the interior of the laparoscopic sealing cover or plug 200 so as to provide still further flexibility of the laparoscopic sealing cover or plug 100A. The second, relatively narrower segment 215 may, in a rest position of the laparoscopic sealing cover or plug 200, be slightly V-shaped or may be closed and converge to bottom 216.

Figure 7:
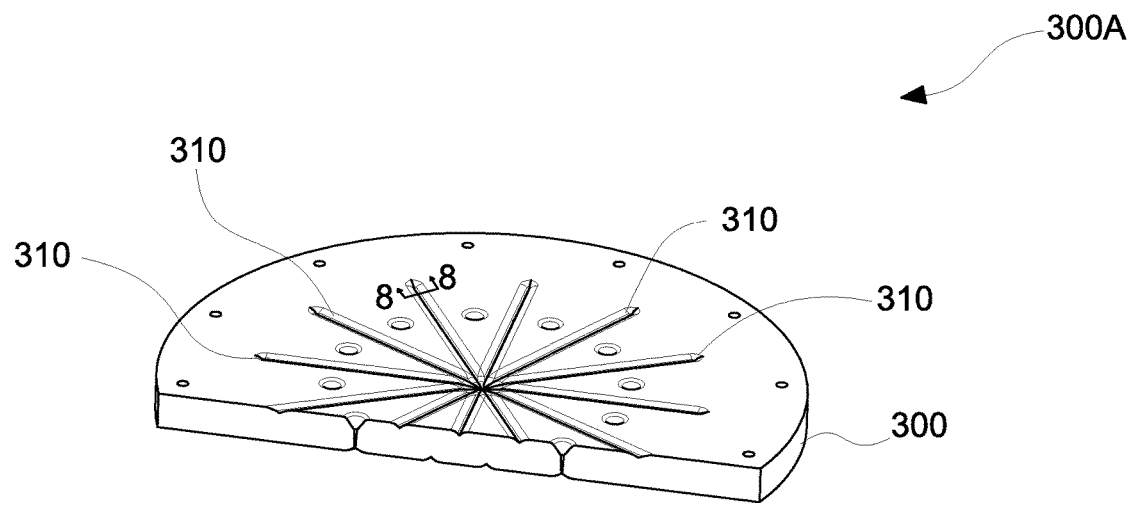
FIG. 7 is a perspective view in partial cross-section of a hand or instrument access surgical site seal cover or plug according to another exemplary embodiment of the present disclosure.
Figure 8:
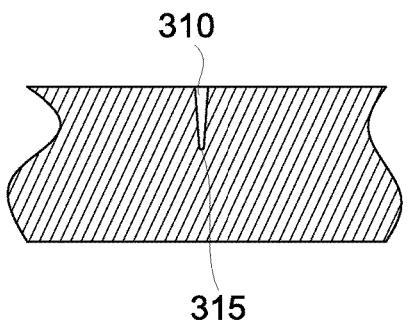
FIG. 8 is an enlarged cross-sectional view taken along the lines 8-8 of FIG. 7 illustrating the configuration of the first and second channels of FIG. 7.

FIG. 7 illustrates a top perspective view of a laparoscopic sealing cover or plug 300A, according to another exemplary embodiment of the present disclosure. The laparoscopic sealing cover or plug 300A is similar to the embodiments previously described hereinabove—however, in this embodiment, the channels 310 define a slight taper or elongate V-shape, e.g., almost substantially linear in configuration, and terminating at an apex 315 such that, in a rest position, they are nearly closed (the channels, in other embodiments, may be completely closed, e.g., the opposing side walls that define the channels may touch each other when the laparoscopic sealing cover or plug 300A is in a rest position). These different channel configurations may further increase the flexibility and structural integrity of the laparoscopic sealing cover or plug 300A.

Figure 9:
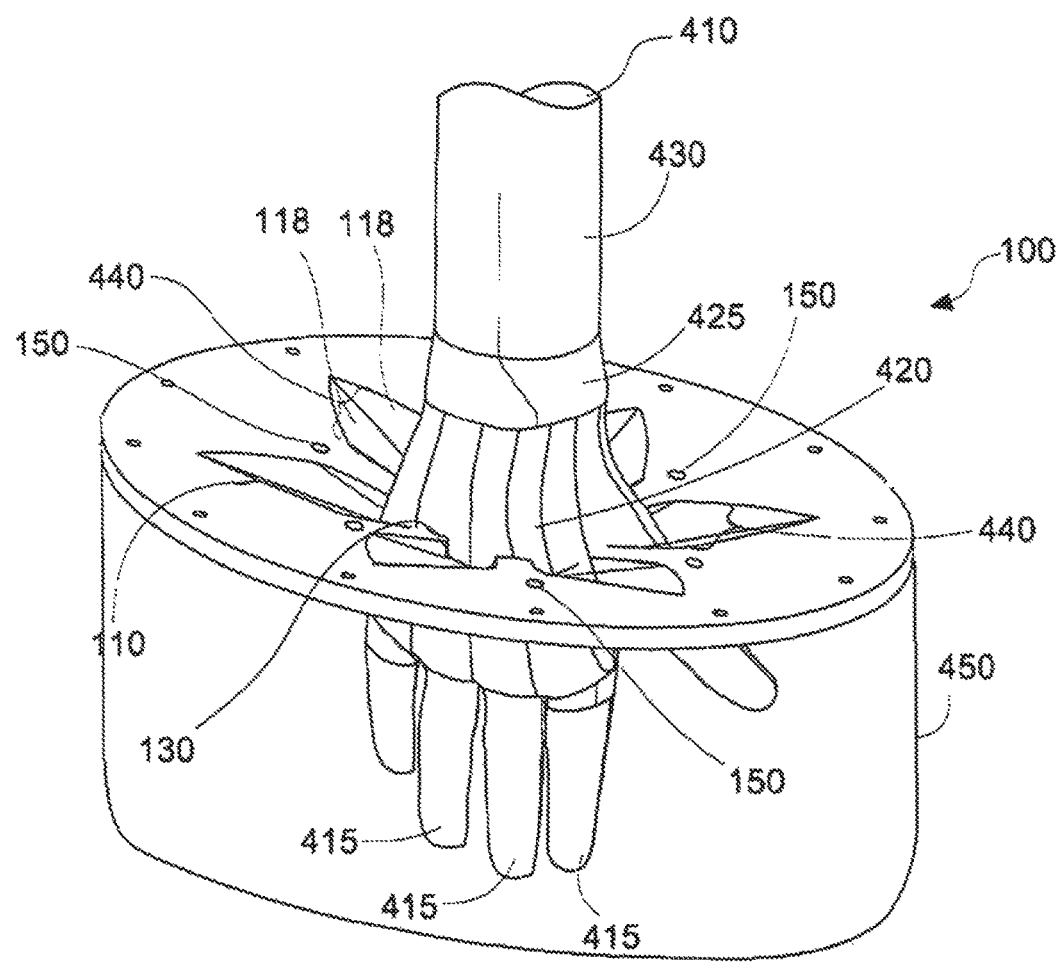
FIGS. 9-10 are perspective views illustrating introduction of a patient's arm through the pleated seal body.
Figure 10:
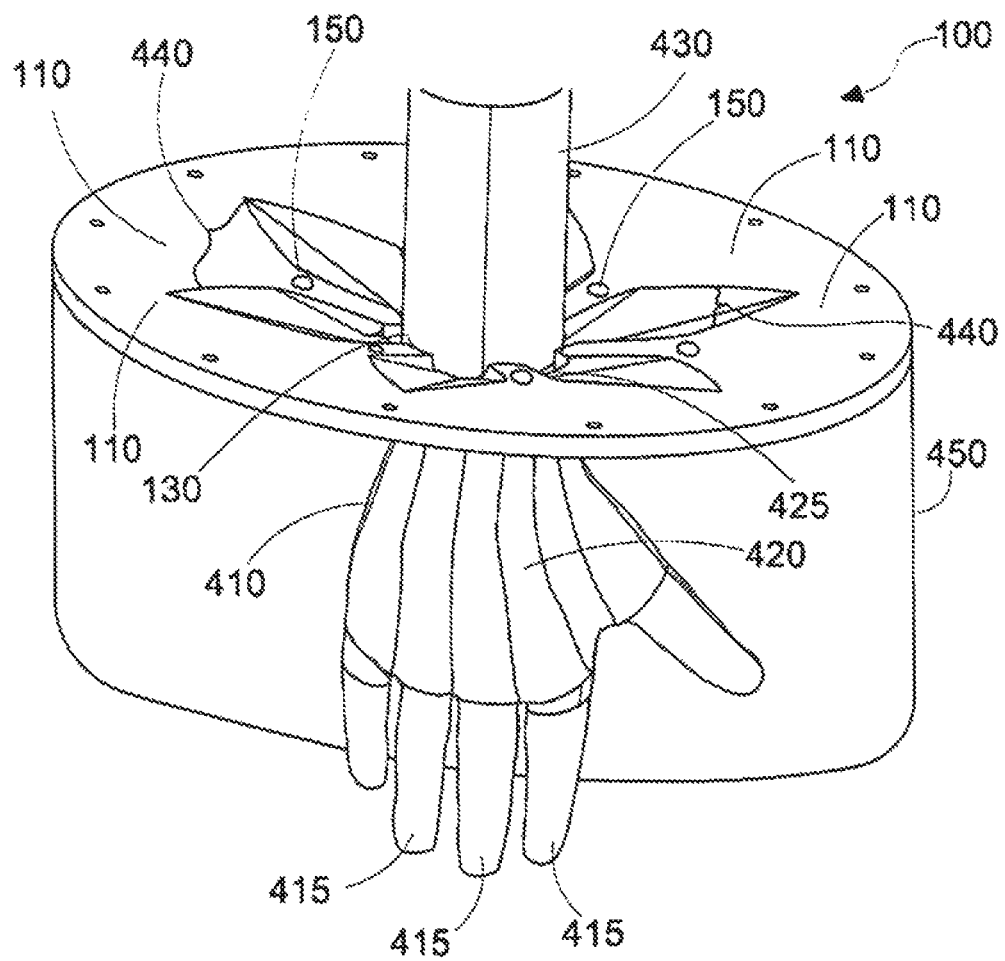

FIGS. 9-10 illustrate an arm 410 extending through the laparoscopic sealing cover or plug, e.g., the laparoscopic sealing cover or plug 200A of FIGS. 5-6 having the opening 230. FIG. 9 depicts the fingers and palm of a hand of the clinician initially introduced within the opening 230. As the fingers pass through the opening 230, the opening 230 stretches in, e.g., an accordion-like manner as facilitated by the pleated configuration provided by the first and second channels 210, 220. For example, the channels 210, 220 expand to accommodate passage of the hand, and may also contract once the hand passes through the seal opening 230 to maintain the seal about the arm. FIG. 10 illustrates the seal opening 230 expanded to accommodate the arm of the clinician. It is noted that FIGS. 9-10 further illustrate schematically a housing 450, which may be a wound retractor or a wound retractor in combination with a proximal stiffening ring. It is contemplated that the laparoscopic sealing cover or plug 100A is selectively attachable/detachable to a housing 450 in order to form a hand or instrument access assembly.

In operation, as illustrated in FIGS. 9-10, as the user (e.g., a surgeon) inserts his/her fingers 415, palm 420, wrist 425, and forearm 430 through the opening 130 of the seal 200, the seal 200 deforms in an accordion-like manner. The deformation may be an expansion/contraction of the individual channels 210, 220 as various portions of the arm 410 are inserted through the opening 230 of the seal 200. The expansion/contraction action occurs to the first surface 218 of each channel 110. Thus, the width of each channel 210 is expanded to accommodate the arm 410. The channels 110 on the top surface 205 expand and/or flex in order to enable the central opening to more easily accommodate the hand 420 and maintain a secure sealing relationship between the hand 420 and the opening 230. The channels 220 on the bottom surface 207 may likewise expand and/or flex when the hand 420 is accommodated in the opening 230. The off-centered or offset relationship between the plurality of first channels 210 and the plurality of second channels 220 allows for the creation of an accordion-like deformation 440 of the seal 200 as an object (e.g., an arm 410) is inserted through the opening 230.

Figure 11:
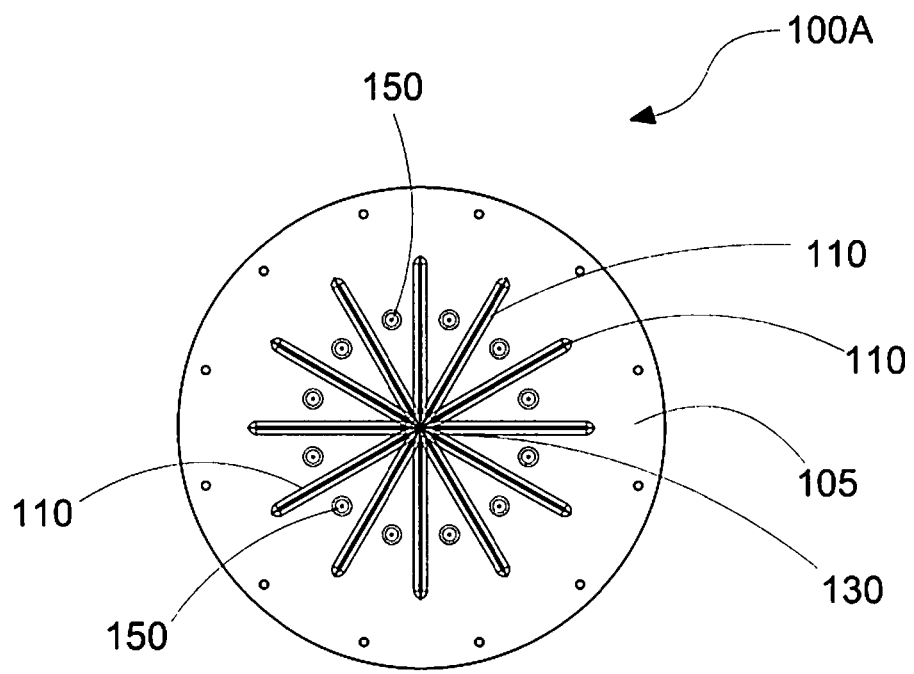
FIGS. 11-12 are top plan views of the seal in closed and open positions respectively.
Figure 12:
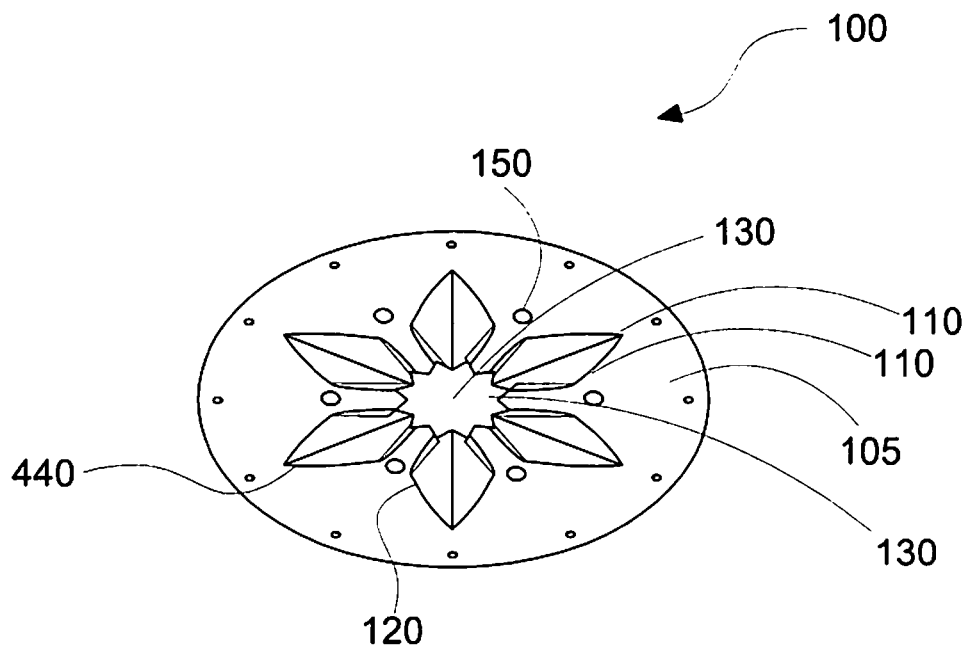

FIGS. 11-12 illustrate such accordion-like deformation 440. FIG. 11 is a top view 500A of the laparoscopic sealing cover or plug 200 in a closed, rest configuration. FIG. 12 is a top view 500B of the laparoscopic sealing cover or plug 200 in a biased configuration. Each of the plurality of channels 210 is deformed to a biased or expanded condition due to the insertion of an object (e.g., an arm 410, not shown) in opening 230. This deformation 440 is characterized as an accordion-like deformation due to the expansion/contraction of channels 210, 220.

This pleated or undulating cross-sectional arrangement may incorporate any number of channels on the top and bottom surfaces of the seal to create a plurality of different patterns thereon. By off-centering the channels of the top surface from the channels of the bottom surface, the probability of tearing the seal is reduced and the laparoscopic sealing cover or plug has improved flexibility to accommodate passage and movement of an instrument and/or hand/arm.

Figure 13:
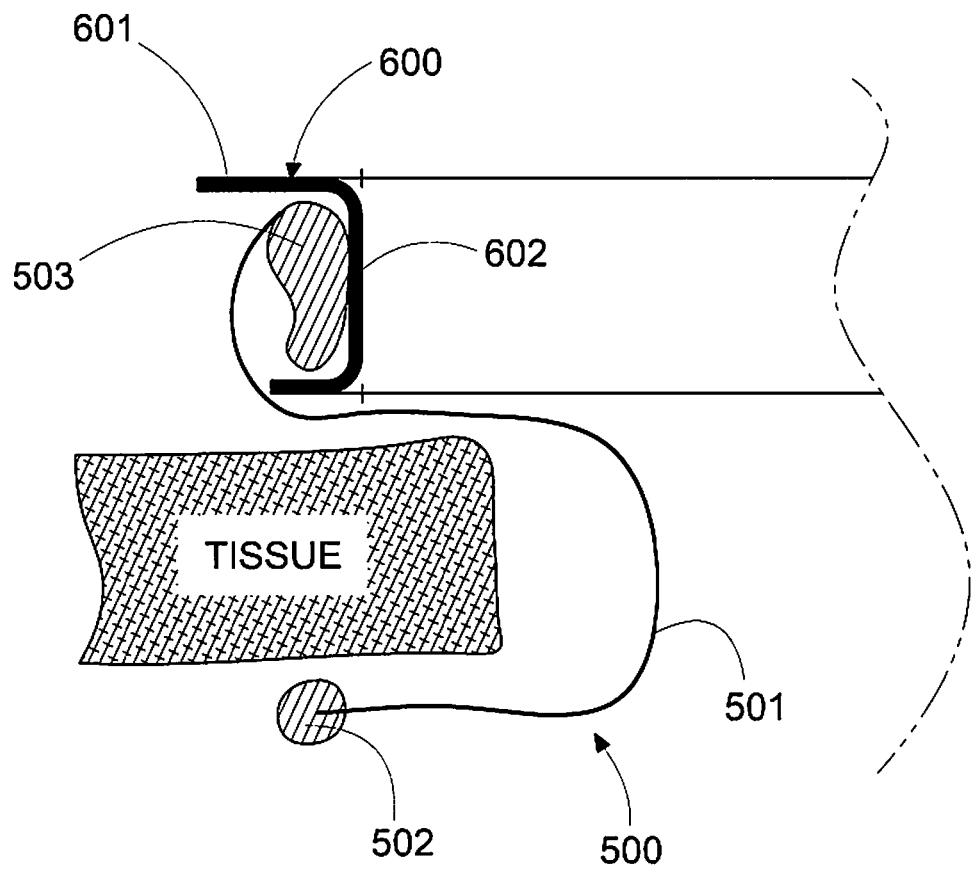
FIG. 13 is a side partial cross-sectional view of a wound retractor having a stiffening ring to which the laparoscopic sealing covers or plugs may be mounted, according to various embodiments of the present invention.

As set forth above, the laparoscopic sealing cover or plug may be mounted to a housing, such as a wound retractor or a separate stiffening ring used in combination with a wound retractor. FIG. 13 is a side partial cross-sectional view of a wound retractor having a stiffening ring to which the laparoscopic sealing covers or plugs may be mounted, according to various embodiments of the present invention. For example, FIG. 13 illustrates a wound retractor 500 that includes a distal ring 502 for positioning through an incision for placement inside a body wall and against an interior surface of a body wall, a proximal ring 503 for positioning outside of the body wall and a flexible sleeve 501 connecting the distal and proximal rings 502, 503, the sleeve 501 configured to be rolled around the proximal ring 503 so as to shorten the length of the sleeve 501 and thereby generate a refraction force to retract the incision. FIG. 13 also illustrates a stiffening ring 600 that assists with maintaining the proximal ring 503 in a circular shape. In various embodiments, the laparoscopic sealing covers or plugs may be selectively mounted directly to the stiffening ring 600 so as to be attached and/or detached as desired by the user. In various embodiments, the seal body may engage, e.g., by friction-fit or any other method of engagement, a radial inward-facing surface 602 of the stiffening ring 600 such that a compression force creates a seal between the stiffening ring 600 and the seal body. Additionally or alternatively, the seal body may engage, e.g., by friction-fit or any other method of engagement, an upper flange 601 of the stiffening ring 600 such that a seal between the stiffening ring 600 and the seal body is created at this location.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Persons skilled in the art will understand that the various covers or plugs, and corresponding methods of use described herein, and shown in the accompanying drawings, constitute non-limiting, exemplary embodiments of the present disclosure, and that additional components and features may be added to any of the embodiments discussed herein above without departing from the scope of the present disclosure.

Additionally, persons skilled in the art will understand that the elements and features shown or described in connection with one exemplary embodiment may be combined with those of another embodiment without departing from the scope of the present disclosure, and will appreciate further features and advantages of the presently disclosed subject matter based on the above-described embodiments and the claims. Accordingly, the present disclosure is not limited by what has been particularly shown and described.

What is claimed is:

1. A hand or instrument access assembly comprising:
   a housing; and
   a seal body mounted to the housing, the seal body having a first proximal surface and a second distal surface opposing the first proximal surface, the seal body defining a substantially centrally disposed opening extending through the first proximal surface and the second distal surface, and second openings for sealed reception of an instrument therethrough;
   the first proximal surface having a plurality of first channels extending radially outwardly from the substantially centrally disposed opening and coterminous therewith and the second distal surface having a plurality of second channels extending radially outwardly from the substantially centrally disposed opening and coterminous therewith, the plurality of first channels being radially offset relative to the plurality of second channels, wherein the plurality of first and second channels are separate and distinctly formed from one another, at least one of the second openings being positioned in between at least two of the first channels of the plurality of first channels.

2. The hand or instrument access assembly according to claim 1, wherein the plurality of first channels have a first width and the plurality of second channels have a second width, the first width being equal to the second width.

3. The hand or instrument access assembly according to claim 1, wherein the plurality of first channels have a first width and the plurality of second channels have a second width, the first width being different than the second width.

4. The hand or instrument access assembly according to claim 1, wherein the plurality of first channels and the plurality of second channels each form a star-shaped configuration.

5. The hand or instrument access assembly according to claim 1, wherein the plurality of first channels and the plurality of second channels are configured to deform in an accordion-like manner to accommodate a hand or an instrument introduced therein.

6. The hand or instrument access assembly according to claim 1, wherein the seal body is formed of foam.

7. The hand or instrument access assembly according to claim 6, wherein the seal body is formed of a monolithic piece of foam.

8. The hand or instrument access assembly according to claim 1, wherein the housing is a wound retractor.

9. The hand or instrument access assembly according to claim 8, wherein the wound retractor includes a distal ring for positioning through an incision for placement inside a body wall and against an interior surface of the body wall, a proximal ring for positioning outside of the body wall and a flexible sleeve connecting the distal and proximal rings, the sleeve configured to be rolled around the proximal ring so as to shorten the length of the sleeve and thereby generate a retraction force to retract the incision.

10. The hand or instrument access assembly according to claim 9, wherein the housing further comprises a stiffening ring that assists with maintaining the proximal ring in a circular shape, the seal body mounted directly to the stiffening ring.

11. The hand or instrument access assembly according to claim 1, wherein the substantially centrally disposed opening is closed in a rest position and configured to inhibit the escape of insufflation gas therethrough when no hand or instrument is inserted.

12. The hand or instrument access assembly according to claim 1, wherein at least a portion of one of the second openings is molded so as to be closed until reception of the instrument therethrough, which tears the material to fully form the opening.

13. The hand or instrument access assembly according to claim 1, wherein at least a portion of one of the second openings includes a pre-formed slit that, in a rest position, is closed.

14. The hand or instrument access assembly according to claim 1, wherein each of the first and second channels are partially configured to be normally closed to inhibit passage of fluids therethrough.

15. A hand access assembly for performing a laparoscopic surgical procedure, the assembly comprising:
a seal body defining a central longitudinal axis and having a first proximal surface and a second distal surface, and defining a first opening extending through the first proximal surface and the second distal surface for reception of a hand, and a second opening for sealed reception of an instrument therethrough, the seal body having a plurality of first channels within the first proximal surface and extending radially outwardly relative to the opening and a plurality of second channels within the second distal surface and extending radially outwardly relative to the opening, the plurality of first and second channels being radially offset with respect to each other and the longitudinal axis, wherein the plurality of first and second channels are separate and distinctly formed from one another, the second opening interposed between two first channels of the plurality of first channels.

16. The hand access assembly according to claim 15, wherein the first channels and the second channels each terminate within the seal body.

17. The hand access assembly according to claim 16, wherein each of the first and second channels have portions configured to be normally closed to inhibit passage of fluids therethrough.

18. The hand access assembly according to claim 15, wherein the second opening is molded so as to be closed until reception of the instrument therethrough, which tears the material to fully form the opening.

19. The hand access assembly according to claim 15, wherein the second opening includes a pre-formed slit that, in a rest position, is closed.

* * * * *